United States Patent
Hovde

(10) Patent No.: US 7,230,711 B1
(45) Date of Patent: *Jun. 12, 2007

(54) ENVELOPE FUNCTIONS FOR MODULATION SPECTROSCOPY

(75) Inventor: David Christian Hovde, Cincinnati, OH (US)

(73) Assignee: Southwest Sciences Incorporated, Santa Fe, NM (US)

(*) Notice: Subject to any disclaimer, the term of this patent is extended or adjusted under 35 U.S.C. 154(b) by 0 days.

This patent is subject to a terminal disclaimer.

(21) Appl. No.: 11/133,803

(22) Filed: May 19, 2005

Related U.S. Application Data

(63) Continuation of application No. 10/364,777, filed on Feb. 10, 2003, now Pat. No. 6,940,599.

(60) Provisional application No. 60/355,862, filed on Feb. 8, 2002.

(51) Int. Cl.
*G01N 21/00* (2006.01)
*G01C 3/08* (2006.01)

(52) U.S. Cl. .................. 356/432; 356/5.09; 356/5.11; 250/343

(58) Field of Classification Search ........ 356/432–440, 356/300, 306–307, 318–319, 326, 5.01, 5.09, 356/5.1, 5.11, 5.15; 250/458.1, 459.1, 343
See application file for complete search history.

(56) References Cited

U.S. PATENT DOCUMENTS

| | | | |
|---|---|---|---|
| 3,899,430 A | 8/1975 | Ancker-Johnson | |
| 4,297,035 A | 10/1981 | Bjorklund | |
| 4,423,519 A | 12/1983 | Bennett, Jr. et al. | |
| 4,485,448 A * | 11/1984 | Kurth | 702/70 |
| 4,577,503 A | 3/1986 | Imaino et al. | |
| 4,703,462 A | 10/1987 | Woodsum | |
| 4,765,736 A | 8/1988 | Gallagher et al. | |
| 4,797,923 A | 1/1989 | Clarke | |
| 4,874,943 A | 10/1989 | Spencer | |
| 4,934,816 A | 6/1990 | Silver et al. | |
| 5,061,854 A * | 10/1991 | Kroutil et al. | 250/339.14 |
| 5,103,711 A | 4/1992 | Iwase | |
| 5,265,039 A * | 11/1993 | Curbelo et al. | 356/319 |
| 5,267,019 A | 11/1993 | Whittaker et al. | |
| 5,281,907 A | 1/1994 | Hartup et al. | |
| 5,448,071 A * | 9/1995 | McCaul et al. | 250/343 |
| 5,498,875 A * | 3/1996 | Obremski et al. | 250/458.1 |

(Continued)

OTHER PUBLICATIONS

Bomse, David S., et al., "Dual-Modulation Laser Line-Locking Scheme", *Applied Optics*, vol. 30, (1991),2922-2924.

Cassidy, D. T., et al., "Harmonic Detection with Tunable Diode Lasers—Two-Tone Modulation", *Applied Physics*, vol. B 29, (1982),279-285.

(Continued)

*Primary Examiner*—Sang H. Nguyen
(74) *Attorney, Agent, or Firm*—Jeffrey D. Myers; Peacock Myers, P.C.

(57) ABSTRACT

A spectrometer and spectrometry method comprising modulating a light source with a carrier waveform multiplied by an envelope function, directing light from the light source through a sample region and to a photodetector, and demodulating current from the photodetector at a reference frequency. Also a method for computing a modulation waveform comprising specifying a target detection efficiency in a Fourier space, computing a response of a waveform that comprises a carrier wave multiplied by an envelope function, and modifying the envelope function using nonlinear optimization means to minimize a difference between the computed response and a predetermined target detection efficiency.

16 Claims, 8 Drawing Sheets

U.S. PATENT DOCUMENTS

| | | | |
|---|---|---|---|
| 5,636,035 A | | 6/1997 | Whittaker et al. |
| 5,640,245 A | * | 6/1997 | Zybin et al. ............... 356/437 |
| 5,694,414 A | * | 12/1997 | Smith et al. ............... 375/130 |
| 5,973,782 A | | 10/1999 | Bomse |
| 6,351,309 B1 | | 2/2002 | Bomse et al. |
| 6,356,350 B1 | | 3/2002 | Silver et al. |
| 6,611,335 B1 | | 8/2003 | Hovde |

OTHER PUBLICATIONS

Fried, Alan, et al., "Reduction of Interference Fringes in Small Multipass Absorption Cells by Pressure Modulation", *Applied Optics*, vol. 27, No. 7, (Mar. 1, 1990),900-902.

Gudeman, C. S., et al., "Tone-Burst Modulated Color-Center-Laser Spectroscopy", *Optics Letters*, vol. 8, No. 6, (Jun. 1983),310-312.

Iguchi, Toshio, "Modulation Waveforms for Second-Harmonic Detection with Tunable Diode Lasers", *J. Optical Society, Am. B*, vol. 3, No. 3, (Mar. 1986),419-423.

Kluczynshi, Pawel, et al., "Theoretical Description Based on Fourier Analysis of Wavelength-Modulation Spectrometry in Terms of Analytical and Background Signals", *Applied Optics*, vol. 38, No. 27, (Sep. 20, 1999),5803-5815.

Pavone, F. S., et al., "Frequency- and Wavelength- Modulation Spectroscopies: Comparison of Experimental Methods Using an AlGaAs Diode Laser", *Applied Physics B 56*, (1993),118-122.

Pickett, Herbert M., "Determination of Collisional Linewidths and Shifts by a Convolution Method", *Applied Optics*, vol. 19, No. 16, (Aug. 15, 1980),2745-2749.

Reid, J., et al., "Second-Harmonic Detection with Tunable Diode Lasers—Comparison of Experiment and Theory", *Applied Physics B 26*, (1981),203-210.

Sasada, Hiroyuki, et al., "Ti-Sapphire Laser Spectrometer for Doppler-Limited Molecular Spectroscopy", *J. Optical Society Am B*, vol. 11, No. 1, (Jan. 1994),191-197.

Silver, Joel A., "Frequency-Modulation Spectroscopy for Trace Species Detection: Theory and Comparison Among Experimental Methods", *Applied Optics*, vol. 31, No. 6, (Feb. 20, 1992),707-717.

Webster, Christopher R., "Brewster-Plate Spoiler: A Novel Method for Reducing the Amplitude of Interference Fringes that Limit Tunable-Laser Absorption Sensitivities", *J. Optical Society Am B*, vol. 2, No. 9, (Sep. 1985),1464-1470.

* cited by examiner

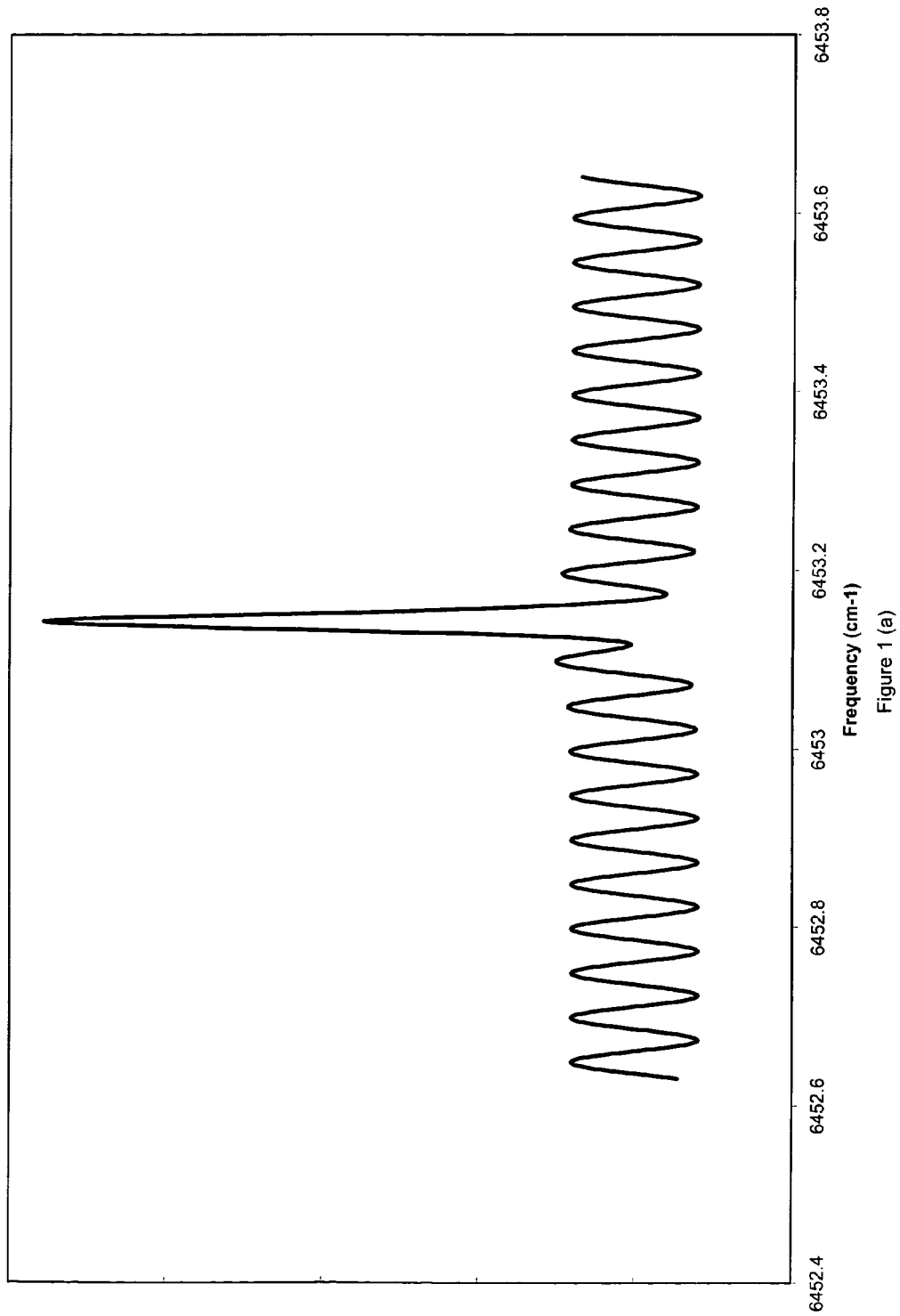

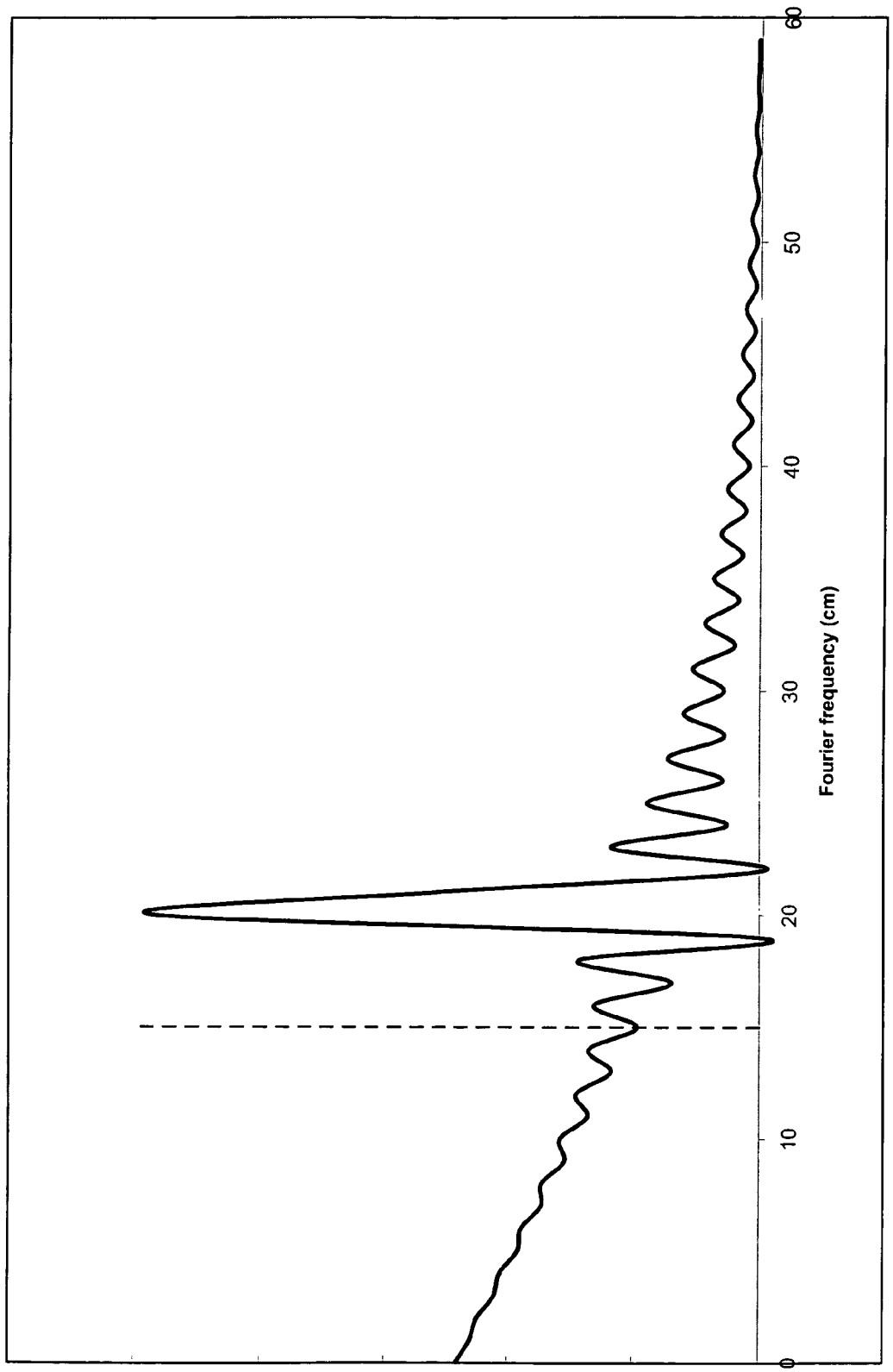

ENVELOPE FUNCTIONS FOR MODULATION SPECTROSCOPY

CROSS-REFERENCE TO RELATED APPLICATIONS

This application claims the benefit of the filing of U.S. Provisional Patent Application Ser. No. 60/355,862 and the specification thereof is incorporated herein by reference.

GOVERNMENT RIGHTS

The U.S. Government has a paid-up license in this invention and the right in limited circumstances to require the patent owner to license others on reasonable terms as provided for by the terms of Contract No. 68-D-99-069 awarded by the U.S. Environmental Protection Agency and contract DG1330-02-CN-0032 awarded by the U.S. Department of Commerce/National Oceanographic and Atmospheric Administration.

BACKGROUND OF THE INVENTION

1. Field of the Invention (Technical Field)

The present invention relates to spectroscopy, in particular to laser modulation spectroscopy.

2. Background Art

Note that the following discussion refers to a number of publications by author(s) and year of publication, and that due to recent publication dates certain publications are not to be considered as prior art vis-a-vis the present invention. Discussion of such publications herein is given for more complete background and is not to be construed as an admission that such publications are prior art for patentability determination purposes.

Absorption spectrometry is a widely used method for measuring the presence or concentration of chemical compounds. Modulation techniques have been widely used to improve the sensitivity of absorption spectrometers. In these techniques, the optical frequency or wavelength of a light source is rapidly varied, or modulated. The modulated light passes through a sample (usually a gas at or below atmospheric pressure) onto a photodetector. The output of the photodetector is amplified as needed, then directed to one or more stages of demodulation or synchronous detection. The demodulation step multiplies the signal from the photodetector by a sine wave whose frequency is related to the modulation frequency or frequencies. The demodulation step is usually implemented with a lock-in amplifier or a radio frequency mixer followed by a low pass filter. Modulation techniques improve sensitivity, in part by exploiting the wavelength dependence of the spectrum of the compound under study and in part because the lasers that are used as light sources typically have less noise at high frequencies. Such noise typically follows a 1/f distribution, where f is the measurement frequency. While modulation techniques can be implemented using an external modulator such as an electro-optic modulator, they are most easily implemented when the light source is a diode laser. Modulating the current used to operate the diode laser modulates its wavelength.

Modulation techniques include wavelength modulation spectroscopy (WMS), frequency modulation spectroscopy (FMS), tone burst spectroscopy (TBS), and two-tone frequency modulation (TT-FMS). These modulation techniques have been described in many publications, for example Pavone et al., "Frequency- and wavelength-modulation spectroscopies: comparison of experimental methods using an AlGaAs diode laser," *Applied Physics* B, 56,118–122 (1993); J. A. Silver, "Frequency Modulation Spectroscopy for Trace Species Detection: Theory and Comparison Among Experimental Methods," *Applied Optics* 31, 707–717 (1991); P. Kluczynski et al., "Theoretical description based on Fourier analysis of wavelength-modulation spectrometry in terms of analytical and background signals," *Applied Optics* 38, 5803–5815 (September 1999); G. Bjorklund, Method and Device for Detecting a Specific Spectral Feature, U.S. Pat. No. 4,297,035 (1981); T. Gallagher et al., Frequency Modulation Spectroscopy Using Dual Frequency Modulation and Detection, U.S. Pat. No. 4,765,736 (1988); D. S. Bomse, Applied Optics 30, 2922–2924; J. Reid and D. Labrie, "Second Harmonic Detection with Tunable Diode Lasers—Comparison of Experiment and Theory," *Applied Physics B* 26, 203–210 (1981).

In the standard wavelength modulation spectroscopy (WMS) approach as applied to diode laser spectroscopy, the laser drive current is modulated with a sine wave. A lock-in amplifier referenced to exactly twice the modulation frequency is used to process the signal from the photodetector. By slowly scanning the laser wavelength, a portion of the absorption spectrum can be recorded. The output of the lock-in amplifier is approximately the second derivative of the absorption spectrum. The peak signals are strongest when the wavelength excursion of the laser is made to be about equal to the width of the spectral features of the gas to be detected, and the exact relationship between signal strength and modulation depth has been worked out for a number of typical spectral line shapes. When, instead, the modulation frequency is made to be about equal to the spectral width, the technique is called frequency modulation spectroscopy (FMS).

In the tone burst spectroscopy method, the light from the laser (or other narrow band source) is transmitted through a sample and onto a detector that produces an electrical output proportional to the transmitted power. The laser's optical frequency or wavelength is modulated at a tone frequency F1 and the modulation is turned on and off at some lower, burst frequency F2. The output of the photodetector, suitably amplified, is measured with a lock-in amplifier referenced to the frequency F2. The output of the lock-in is a measure of the difference in transmission with and without the modulation. Good detection sensitivity is achieved when the modulation depth or modulation frequency is about equal to the width of the targeted spectral transition. Detection at F2 avoids laser 1/f noise at still lower frequencies. Tone burst spectroscopy has been developed by a number of workers. H. M. Pickett, "Determination of collisional linewidths and shifts by a convolution method," *Applied Optics* 19, 2745–2749 (1980), first applied the tone burst method to absorption spectroscopy in microwave experiments. C. S. Gudeman et al., "Tone-burst Modulated Color-center-laser Spectroscopy," *Optics Letters*, Vol. 8, pp. 310–312 (1983), demonstrated the use of tone burst spectroscopy with a color center laser. H. Sassada et al., "Ti-Sapphire Laser Spectrometer for Doppler-limited Molecular-Spectroscopy," *J. Opt. Soc. Amer. B* Vol. 11, pp. 191–197 (1994), notes the close connection between tone burst spectroscopy and two-tone frequency modulation spectroscopy. TTFMS is a variation of FMS that was developed to avoid the need for extremely high frequency detectors and demodulators required for FMS. Two high modulation frequencies are used, F3 and F4, while the demodulation step is referenced to the lower difference F3–F4 between the frequencies. Plotting the TTFMS modulation signal vs. time reveals the close relation of TTFMS to TBS. The high frequency modulation amplitude rises and falls in a slower envelope. The frequency of the envelope is F3–F4. Thus, TTFMS can be thought of as a form of TBS, but with a smooth envelope instead of the on-off step function typically used in TBS.

In practical systems based on WMS, FMS, TBS or TTFMS, the sensitivity is limited by optical noise arising from light scattered or reflected within the optical system. This light coherently beats against the main optical beam at the detector. When a section of the spectrum is scanned, this noise appears as a sinusoidal modulation of the baseline intensity. It is known as an interference fringe or etalon. The period of the fringe depends on the extra time taken for the stray reflection to reach the detector. When measured in units of the spectral wavelength or frequency of the laser it is known as the free spectral range. The amplitude of the fringe depends on the strength of the reflected beam and its overlap with the main beam. By careful design of the optical system, it is possible to reduce the amplitude of such fringes to about 0.001% of the laser intensity. The phase of the fringe is sensitive to small changes in the optical alignment, so it usually varies when the ambient temperature changes.

Although the effect of the fringes is small, so low is the noise from a diode laser spectrometer that one or two orders of magnitude improvement in sensitivity could be achieved if it were possible to suppress them. As a result, several mechanical approaches have been taken to suppress such noise. One can vary the time delay of the stray beam by vibrating the position of an optical element [J. A. Silver and A. C. Stanton "Laser Absorption Detection Enhancing Apparatus and Method," U.S. Pat. No. 4,934,816 (1990)] or by varying the angle of a window [C. R. Webster, "Brewster-Plate Spoiler: a Novel Method for Reducing the Amplitude of Interference Fringes that Limit Tunable Diode Laser Absorption Sensitivities," *J. Optical Society of America B* 2, 1464–1470 (1985)], then average over the various delays. When the time delay is of the order of a half optical cycle or more of the light, the phase of the fringe varies by 180 degrees or more and these methods are effective. However, these approaches require mechanically changing the position of an optic, incurring the cost of an actuator. One can vary the pressure of the sample [A. Fried et al., "Reduction of Interference Fringes in Small Multipass Absorption Cells by Pressure Modulation," Applied Optics 29, 900–902 (1990)], which may act to vary the delay either mechanically or by changing the index of refraction. Alternatively, the sample dependent part of the signal can be extracted by suitable analysis of its pressure dependence. This approach involves an actuator to vary the sample pressure and requires a pumping system to add or remove gas. As it is difficult to rapidly vary the pressure, this approach may not be suitable when a fast response is desired from the instrument.

Variations of both the WMS and FMS approaches have been developed to reduce optical noise. D. S. Bomse et al., "Dual-Modulation Laser Line-Locking Technique For Wavelength Modulation Spectroscopy," U.S. Pat. No. 6,351,309 (2002); D. S. Bomse, "Dual-Modulation Laser Line-Locking Scheme", Applied Optics, 30 (1991) reported an approach in which two modulation frequencies are added to the bias current, and the signal is demodulated sequentially at a harmonic of each. E. A. Whittaker et al., "Method and apparatus for reducing fringe interference in laser spectroscopy", U.S. Pat. No. 5,267,019 (1993) and "Method and apparatus for dual modulation laser spectroscopy," U.S. Pat. No. 5,636,035 (1997) reported another approach. These approaches have the drawback that the phases of two demodulation steps must be adjusted to achieve high sensitivity and calibration stability. They have the further drawback that the peak modulation amplitude can be twice as large as for standard WMS or FMS.

D. T. Cassidy and J. Reid, "Harmonic Detection with Tunable Diode Lasers—Two-Tone Modulation," *Applied Physics B* 29, 279–285 (1982) employ WMS with the addition of a second modulation frequency, but without a second demodulation step. The amplitude of this second modulation, termed a jitter modulation, is chosen to minimize the detection of particular fringe, and it may be quite small. They show that the detection sensitivity for a given fringe depends on the amplitudes of each modulation waveform and on the period of the fringe, in particular as the product of two Bessel functions. The amplitude of the first modulation is adjusted to maximize detection of the target absorption signal, while the amplitude of the second modulation is chosen to minimize detection of the interfering optical fringe. This approach is especially useful when the free spectral range of the fringe is smaller than the width of the spectral feature to be detected. A disadvantage of this approach is that the free spectral range of the fringe must be known, and it is not useful for eliminating more than one fringe.

The use of non-sinusoidal modulation waveforms in WMS reduces the sensitivity to fringes. T. Iguchi, "Modulation Waveforms for Second Harmonic Detection with Tunable Diode Lasers," *J. Optical Society of America B*, 3, 419–423 (1986), compared sine wave modulation, square wave modulation, quasi-square wave modulation, triangular wave modulation, and an inverse integral raised cosine (IIRC) waveform. The best waveform is one that is sensitive to the Fourier components of the signal but insensitive to fringes outside this range. Generally, the waveforms with sharp tips showed less sensitivity to etalons with small free spectral range. Triangle waves give a good response and the IIRC waveform is even better. However, Iguchi noted that the IIRC waveform extends to infinity, so it is impractical for a realistic instrument. Iguchi also considered the use of jitter waveforms of various shapes together with the various modulation waveforms. Adding a jitter modulation produces a weighted average or blurring of the spectrum, with the weighting function determined by the jitter amplitude and shape. The jitter approach was found not to work when the free spectral range of the fringe was comparable to or larger than the line width of the signal.

The present invention provides a means of minimizing fringes over a wide range of free spectral ranges, while optimizing the detection of a target signal. The present invention also provides a method to compute modulation waveforms that minimize the detection of fringes or that optimize the detection of signals of arbitrary shape.

SUMMARY OF THE INVENTION
(DISCLOSURE OF THE INVENTION)

The present invention is of a spectrometer and spectrometry method, comprising: modulating a light source with a carrier waveform multiplied by an envelope function; directing light from the light source through a sample region and to a photodetector; and demodulating current from the photodetector at a reference frequency. In the preferred embodiment, the shape of the envelope function operates to selectively detect predetermined Fourier components of a spectrum. The reference frequency is equal to: (1) the frequency of the carrier waveform or an integer multiple thereof; or (2) the frequency of the envelope function. The light source is preferably a laser, most preferably a diode laser. Demodulating is performed by lock-in amplifier or radio frequency mixer. One preferred envelope function comprises a polynomial function of order greater than two. The time constant employed by the demodulating means is at least as long as the period of the envelope function.

The invention is also of a method for computing a modulation waveform, comprising: specifying a target detection efficiency in a Fourier space; computing a response of a waveform that comprises a carrier wave multiplied by an envelope function; and modifying the envelope function using nonlinear optimization means to minimize a difference between the computed response and a predetermined target gain spectrum. In the preferred embodiment, the target gain spectrum comprises a signal band and a stop band.

A primary object of the present invention is to permit sensitive detection of an atomic or chemical species by modulation spectroscopy without loss of sensitivity by interference from fringes.

Another object is to select for detection only those components of the signal for which the signal to noise ratio is favorable.

BRIEF DESCRIPTION OF THE DRAWINGS

FIG. 1(a) shows a computed absorption feature of carbon dioxide and a fringe over a spectral interval of about 1 cm-1. FIG. 1(b) shows the Fourier transform of the absorbance spectrum. The sharp peak in the Fourier spectrum is due to the fringe. The desired cutoff point is indicated.

DESCRIPTION OF THE PREFERRED EMBODIMENTS

Figure 2:
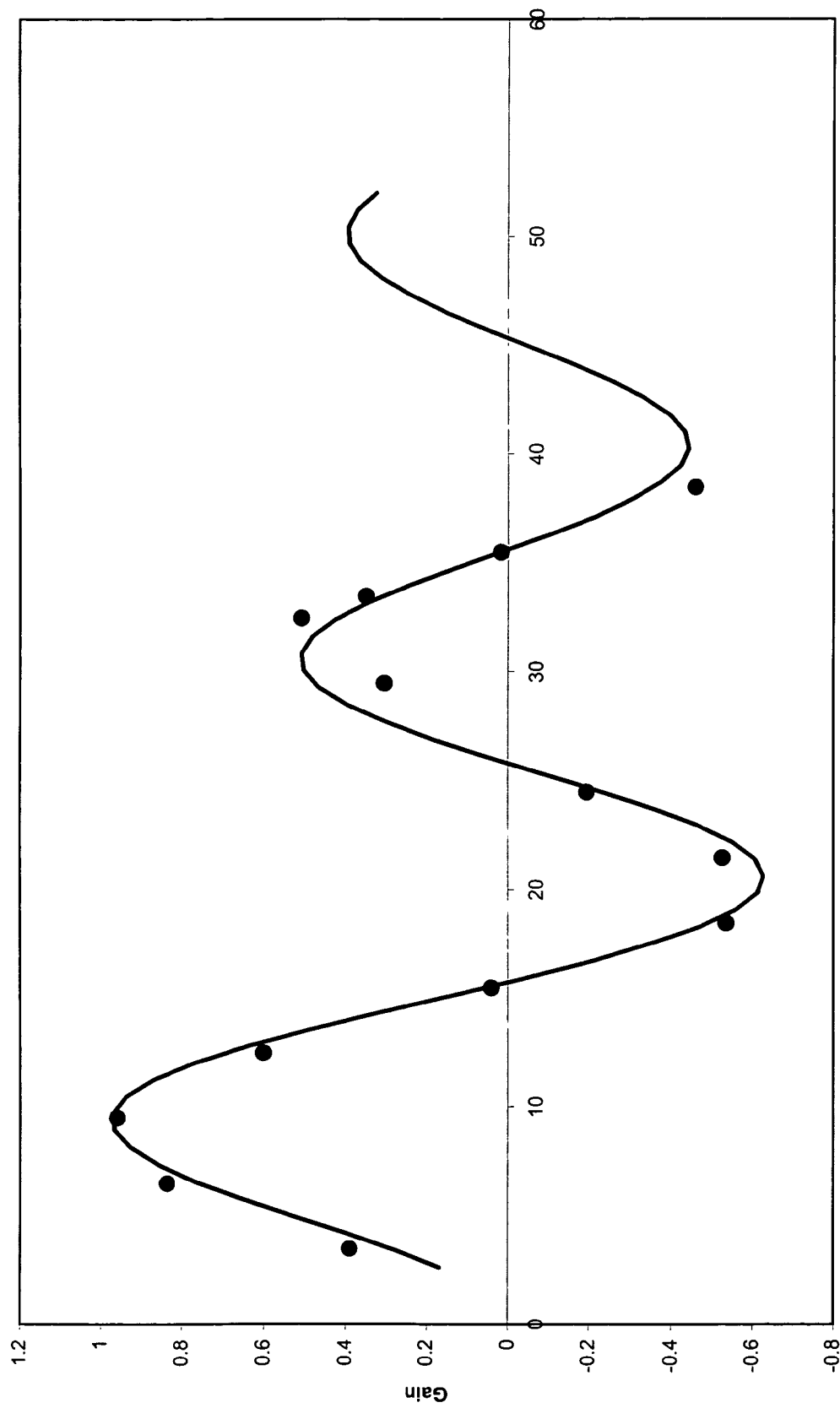
FIG. 2(a) shows the computed detection efficiency (curve) for wavelength modulation using a constant amplitude sine wave and detection at twice the modulation frequency, and the measured detection efficiency (symbols).
FIG. 2(b) shows the computed (curve) and measured (symbols) detection efficiency as in (a), but where the modulation amplitude has been multiplied by an envelope function to minimize detection of fringes with large path difference.
FIG. 2(c) shows the computed (curve) and measured (symbols) detection efficiency for tone burst modulation, in which the tone waveform has been multiplied by an envelope function designed to minimize detection of fringes with a large path difference.
Figure 2:
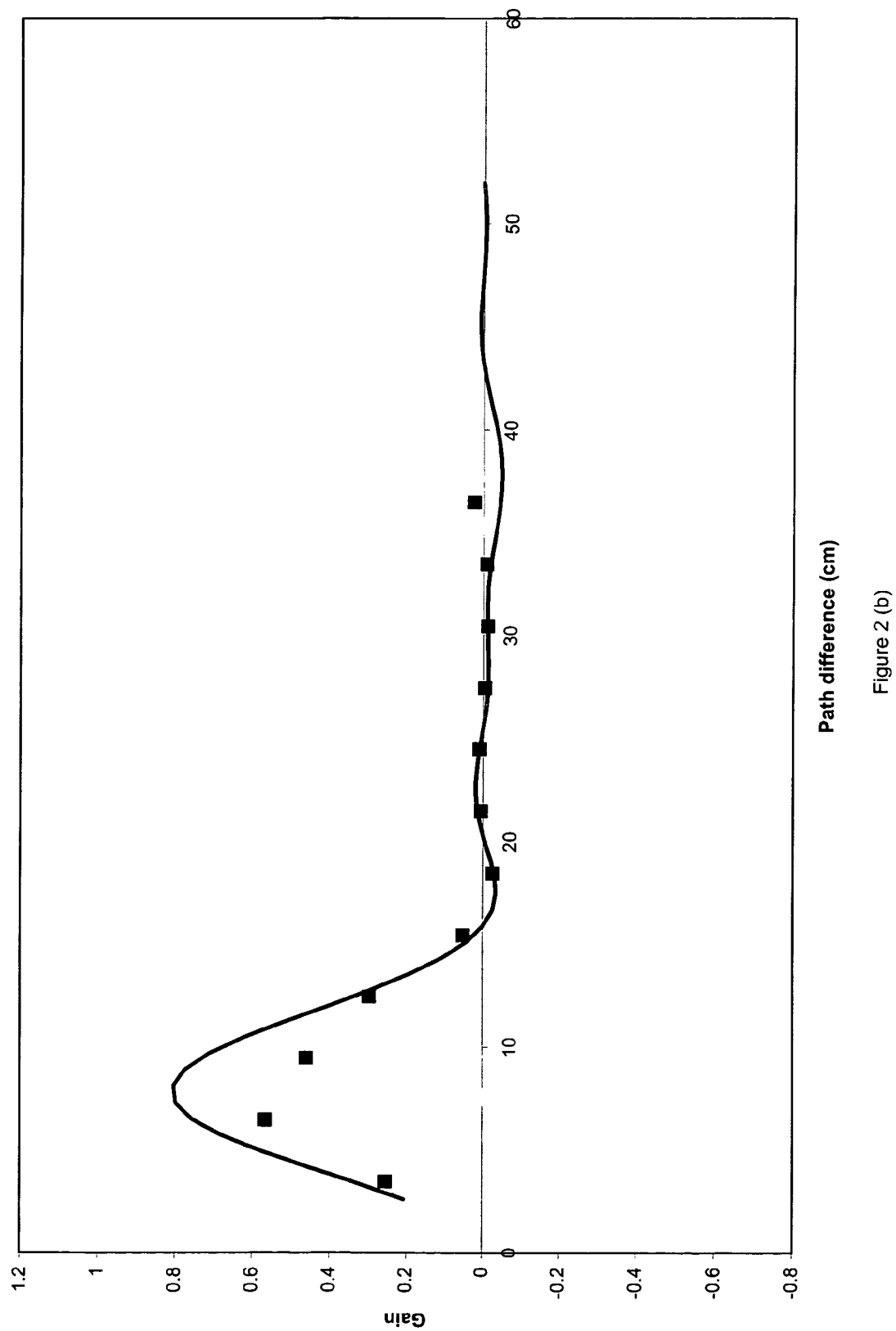
Figure 2:
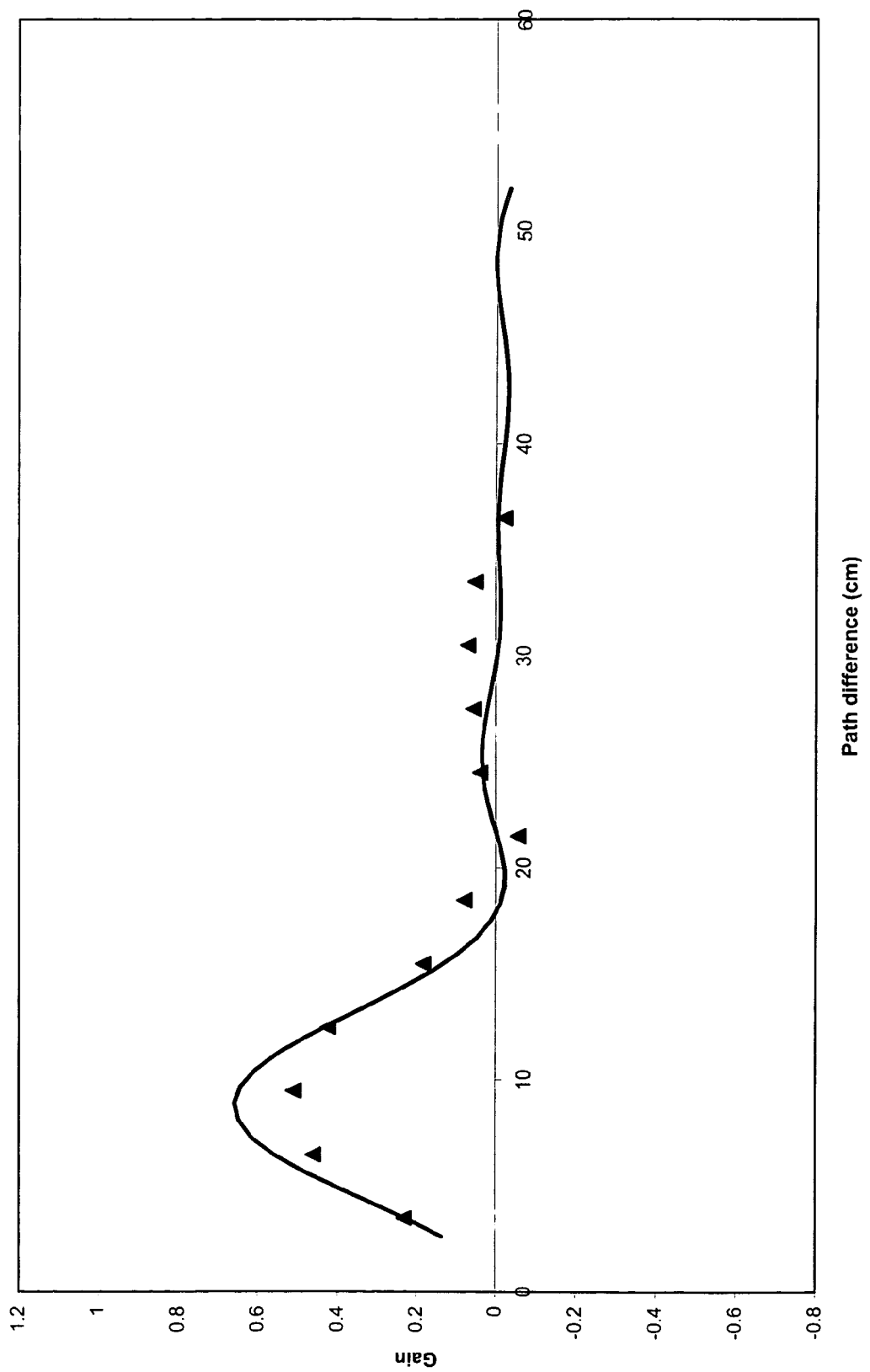

Best Modes for Carrying Out the Invention

The present invention is an apparatus for and a method of preferentially detecting only those Fourier components of a spectrum that convey the most information. It employs a modulation circuit, a light source whose wavelength or frequency can be modulated, a sample path, a photodetector, and a demodulator. The modulation circuit produces a waveform, such as a sine wave or triangle wave, multiplied by an envelope function. The invention also comprises a method of modulating the light source of a spectrometer in a way to optimize the detection of certain Fourier components of a spectrum under investigation. The modulation waveform is multiplied by an adjustable envelope function. The lock-in amplifier time constant is set to be longer than the characteristic period of the envelope function. The envelope function is adjusted to give the desired performance through an optimization algorithm.

The advantages of the present invention can be obtained with any spectrometer that can be rapidly wavelength modulated with a modulation depth comparable to the characteristic line width of the spectral feature to be detected. This includes laser systems with external frequency modulators. However, the low cost and ease of modulation of diode lasers make them the preferred light source for most present applications. The following detailed description of the invention as applied to tunable diode laser spectroscopy as used to make sensitive measurements of carbon dioxide and carbon monoxide gas concentrations illustrates the invention.

Because the fringes that interfere with the absorption spectroscopy measurements are approximately sinusoidal, it is easiest to design the modulation waveform by viewing its properties in Fourier space. Fourier transforms are computed using commercial software packages (e.g., LabView, National Instruments, Austin Tex. or like data processing hardware and/or software). The spectrum produced by a diode laser spectrometer typically consists of a scan over a frequency interval of about 1 cm$^{-1}$ that includes a spectral transition. Because spectra may be recorded against frequency or wavelength, the Fourier transform variable will have units of 1/frequency or 1/wavelength. This variable thus has units of 1/FSR (free spectral range) of the etalon. FIG. 1(a) shows a simulation of a 1 cm$^{-1}$ spectral region around 6553 cm$^{-1}$. It includes a single absorption peak of $CO_2$ and a sinusoidal fringe with a 0.05 cm$^{-1}$ FSR. FIG. 1(b) shows the Fourier transform of this spectrum after shifting the $CO_2$ absorption peak position to zero frequency. The narrow peak in Fourier space corresponds to the fringe at a value on the x axis equal to the inverse of its free spectral range. The ringing around the narrow peak is due to the fact that the spectrum does not extend to infinite frequency, resulting in windowing effects. The relatively broad decay from 1/FSR=0 results from the $CO_2$ absorption feature. Because the frequency in FIG. 1(a) is measured in cm$^{-1}$, the Fourier axis has units of cm.

The response of a wavelength modulation spectrometer can be described by describing its response to each Fourier component. For instance, using a sine wave modulation and detecting at twice the modulation frequency, a standard wavelength modulation spectrometer has a detection efficiency for each Fourier component given by $J_2(2\pi E/FSR)$, where $J_2$ is a Bessel function and E is the modulation amplitude. The detection efficiency for this case is plotted against 1/FSR in cm in FIG. 2(a). While this wavelength modulation approach is sensitive to the Fourier components of the $CO_2$ absorption feature, it is also efficient at detecting Fourier components outside the range of the gas absorption signal. As a result, fringes of many FSRs can be detected and interfere with the measurement. Iguchi shows the absolute value of the detection efficiency for several modulation waveforms and notes that the sensitivity to fringes can be reduced by appropriate choice of a waveform. In particular, choosing a triangle wave or an inverse cosine wave damps the oscillations in the detection efficiency at large values of 1/FSR.

The ideal modulation waveform should detect those Fourier components of the absorption spectrum where the gas signal is strong, while minimizing the detection of fringes that only interfere with the measurement. A mathematical definition for the ideal modulation waveform is one that produces a spectrum with the highest possible signal to noise ratio, or a minimum in the noise to signal ratio. A practical diode laser spectrometer can make only finite modulation excursions without producing nonlinear effects or even destroying the laser, so the ideal modulation waveform must not require excessive modulation amplitude.

The signal to noise ratio will depend on the amplitudes and FSRs of the fringes actually present in an instrument. Without prior knowledge of the amplitudes and FSRs of fringes in an instrument, a simple definition of the ideal modulation waveform is one that has high detection efficiency in the interval between 1/FSR=0 and 1/FSR=15 cm (the signal band), while filtering out or failing to detect Fourier components with 1/FSR of 15 cm and higher (the stop band) where there is a weaker gas signal but there may be fringes. The cut-off point, 15 cm, is related to the spectral width of the $CO_2$ absorption line and to the period of the fringes actually encountered. Using this definition, the signal is proportional to the RMS gain in the signal band. The noise can be estimated as root mean squared values of the detection efficiency in the stop band, plus a small constant that corresponds to shot noise or detector noise. Experience indicates that fringes are usually about two orders of magnitude greater than shot noise in a standard WMS system, so the small constant can be set to about 1% of the RMS in the stop band of a standard sine wave modulation.

In addition to defining an estimate for the signal to noise ratio expected from a modulation waveform based on its detection efficiency as a function of Fourier frequency, it is also necessary to define a penalty for large modulation amplitude. The chosen function in this case is simply the peak value of modulation excursion divided by the desired modulation limit, raised to the fourth power. For excursions less than the limit, this function is small and does not contribute significantly to the total error function. The sum of the noise to signal ratio plus the modulation penalty defines the error function. Other error functions could be defined based on more carefully matching the detection efficiency to the Fourier components of the absorption signal, or using prior knowledge of the FSR of fringes expected to interfere with the measurement, as determined by analyzing the optical design or by test measurements made on the instrument.

The detection efficiency depends on the shape and the amplitude of the modulation waveform. When the amplitude of the modulation is not constant, but consists of a variety of values defined by an envelope function, the detection efficiency will vary. However, when the detection electronics include a low pass filter whose time constant is greater than one period of the envelope function, the filtered detection efficiency will be essentially constant and equal to the detection efficiency averaged over the entire envelope. The error function described above can be calculated for the average detection efficiency. Numerical techniques for the optimization of nonlinear functions can be used to choose an envelope function whose detection efficiency has the smallest error function. A robust but slow technique is simulated annealing. A detailed description of the simulated annealing approach is given, but other nonlinear optimization techniques could be used.

A sinusoidal waveform was selected as the basic modulation. While triangle wave modulation has better rejection of fringes in the stop band, it requires wider bandwidth electronics to implement. Furthermore, a diode laser's tuning properties depend on the details of thermal transport within the laser and mount, so that the current tuning rate may depend on modulation frequency. As a result of these two effects, when a diode laser is excited with a triangle wave, the modulation response might be quite different. In contrast, sine wave excitation will lead to a sine wave response, regardless of the effects of time constants in the electronic or thermal response of the system. The envelope function broadens the modulation bandwidth somewhat, but the bandwidth is small compared to that for triangle wave modulation. The small bandwidth makes it easier to calibrate the modulation and the more ideal laser behavior makes the calculation of the optimum modulation envelope more exact.

The modulation envelope function should be flexible but contain just a few parameters, to simplify the search for a minimum. For the case of sculpted wavelength modulation, a third-order polynomial envelope was chosen. The envelope was constructed by multiplying the four parameters with powers of an array of 128 real numbers that were evenly distributed in the range from −1 to 1. Calling the envelope function E and the array X, $$E_i = aX_i^0 + bX_i + cX_i^2 + dX_i^3 \qquad (1)$$

The subscript i runs over the 128 real values of X. Adjusting the four parameters a, b, c, and d thus adjusts the envelope function. The modulation waveform is constructed by multiplying a single cycle of a unit sine wave times a single value $E_i$ of the envelope function. The envelope function does not vary during the modulation cycle.

The output of the demodulator is filtered with a time constant that should be at least as long as a single period of the envelope function. For such a time constant, the output represents the average signal over the envelope function. As a result of the construction, each cycle of the modulation waveform is still truly sinusoidal, so existing wavelength modulation theory can be used to compute the response to fringes. For the case where the demodulator is set to detect the signal at twice the modulation frequency, the sensitivity to a given fringe is $$S = \Sigma_i J_2(2\pi E_i/FSR) \qquad (2)$$

Computing S over a range of values of 1/FSR yields the detection efficiency for the modulation envelope E(a, b, c, d).

Figure 5:
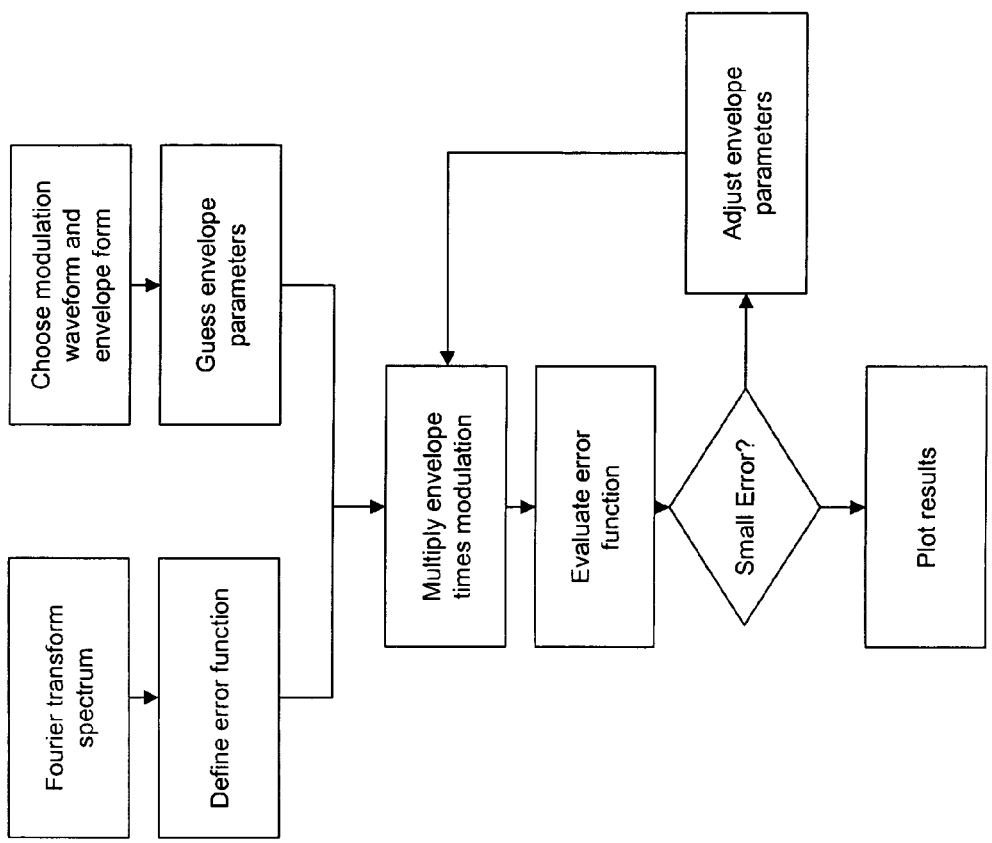
FIG. 5 shows the steps involved in optimizing the envelope function that multiplies the modulation waveform.

The simulated annealing process to find the best envelope to match the target gain spectrum begins by making a guess for the starting values for the envelope functions, as shown in FIG. 5. The program also requires a guess for the starting values of the desired changes in the envelope functions and an estimate of the starting "temperature" of the fit, set equal to 3 by trial and error. The temperature is used as described below to determine whether to accept or reject a new guess for the envelope that has a poorer error function than the previous guess. This feature of simulated annealing prevents the fit from being trapped in local minima that have barriers on the order of the temperature parameter.

The fit computes the error function for the initial guess by computing the detection efficiency for a unitless 1/FSR ranging from 0 to 1. The cutoff point is later adjusted by changing the voltage gain of the digital waveform synthesizer. The gain values in the signal and stop bands, together with the maximum value of the modulation, are used to evaluate the error function. The fitting program then begins a "Markov chain", in which all the parameters for the envelope function are modified by adding to them the step parameter multiplied by a normal Gaussian variable. The error function is calculated for the new envelope. The new envelope is accepted if the error function is less than that of the old envelope. It is also accepted if $$\exp\left(\frac{error_{old} - error_{new}}{T}\right) \geq r$$

where r is a random number uniformly distributed on the interval from 0 to 1. When the error function for the new guess is not much worse than the previous guess, the exponential function is about equal to 1, and the odds of accepting the state are high. The temperature parameter determines the probability of accepting a new guess that has a higher error function than the old.

The Markov chain continues testing new guesses, comparing each new guess to the most recently accepted guess, until 100 guesses have been accepted or until 500 guesses have been tried. At the end of one chain, the step vector is adjusted, using statistics acquired from the successful guesses, according to the algorithm given by Corann. If the number of accepted guesses is between 40% and 60% of the total number of guesses, then the temperature is decreased. If fewer guesses are accepted, then the parameter step vector is decreased, while if too many guesses are accepted the step vector is increased. Then another Markov chain is propagated, beginning at the endpoint of the previous Markov chain. This process continues until the temperature is reduced to 0.001.

Figure 3:
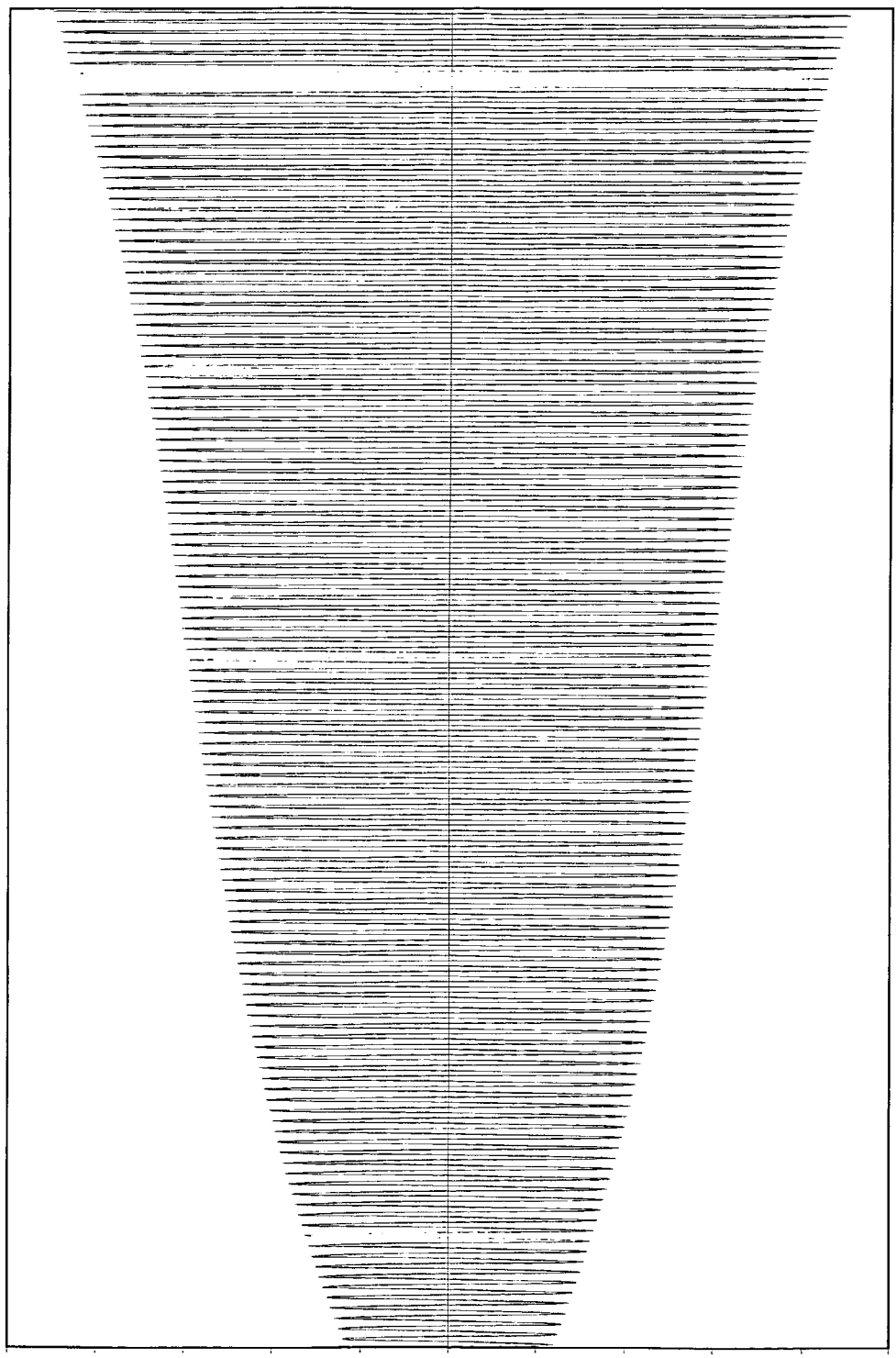
FIG. 3 shows the modulation waveform for wavelength modulation with detection at twice the modulation frequency. The modulation envelope has been optimized to detect signals below the cutoff point given in FIG. 1, while minimizing the detection of signals above the cutoff point.

The optimized detection efficiency determined by simulated annealing is plotted as the line in FIG. 2(b). The symbols in FIG. 2(b) are experimental measurements of the detection efficiency, as described below. The coefficients for the optimized envelope from Equation 1 are a=−2.94, b=−1.10, c=0.08, and d=−0.55. The modulation waveform is plotted in FIG. 3.

One special case for the envelope function is worth noting. A sine wave envelope can be shown to be equivalent to the addition of sine wave modulation, by using the trigonometric identity $\sin\alpha \sin\beta = \frac{1}{2}\cos(\alpha-\beta) - \frac{1}{2}\cos(\alpha+\beta)$ and disregarding the phase of the envelope. In this special case, the envelope function and subsequent demodulation is equivalent to the jitter modulation introduced by Cassidy and Reid.

The procedure for optimizing a tone burst waveform is very similar, except that the envelope function is defined differently and the tone burst sensitivity defined differently. The error function has the same definition, so the signal band and the stop band are the same as for sculpted WMS. The envelope function for tone burst is defined in terms of two polynomials, one that covers the "on" half cycle of the waveform (during which the modulation is switched on to a constant value in conventional tone burst modulation), and the second that covers the "off" half cycle (during which the modulation is switched off in the conventional approach). In the present invention, a single cycle of the tone bust waveform can contain all the values of the envelope function, although equivalent functionality can be obtained by using an envelope function that includes more than one cycle of the tone burst waveform. It is very important that the tone burst waveform allow for the possibility of a non-zero modulation depth during the off cycle. Without this capability, tone burst remains sensitive to fringes in the stop band.

The tone burst envelope function is defined as a second order polynomial for the off cycle and a separate second order polynomial for the on cycle. Even order polynomials were used for both half-cycles. As with the wavelength modulation calculation, the polynomials multiply an array of evenly spaced real numbers ranging from −1 to 1. The envelope function is found by concatenating the two polynomials. There are thus six adjustable parameters corresponding to the coefficients of the $X^0$, $X^2$, and $X^4$ for each half cycle of the envelope:

$E_i = a + b\,X_i^2 + c\,X_i^4$ for the first half cycle, and
$E_i = d + e\,X_i^2 + f\,X_i^4$ for the second half cycle.

The modulation waveform is again found by multiplying one cycle of a unit sine wave times a single envelope value.

For tone burst modulation, the lock-in is referenced to the on-off cycle frequency, or in this case to the envelope frequency. The demodulated output can be found by taking the dot product of the instantaneous transmission during each cycle of the modulation with a sine wave of the same frequency as the envelope function. However, the modulation frequency is much higher than the envelope function and therefore does not contribute significantly to the dot product. A much simpler computation is to evaluate the dc component produced at each value of the envelope function, and take the dot product with a sine wave of this smaller array. The dc component for a particular fringe is just the Bessel function of zero order of the modulation divided by the FSR of the fringe $J_0(2\pi\, E_i/FSR)$. As with the WMS case, the sensitivity is computed for a range of a unitless 1/FSR of 0 to 1.

The simulated annealing algorithm is used to adjust the six coefficients of the envelope function to minimize the error function. The optimized coefficients are a=−2.69, b=−5.52, c=6.59, d=−0.47, e=−7.10, and f=11.41. The resulting optimized detection efficiency is plotted in FIG. 2(c) as a curve. The symbols in FIG. 2(c) are experimental measurements of the detection efficiency.

A special case for tone burst modulation should also be mentioned. When the envelope is a sine wave, the tone burst waveform and subsequent demodulation is equivalent to two tone FMS described by Gallagher.

Figure 4:
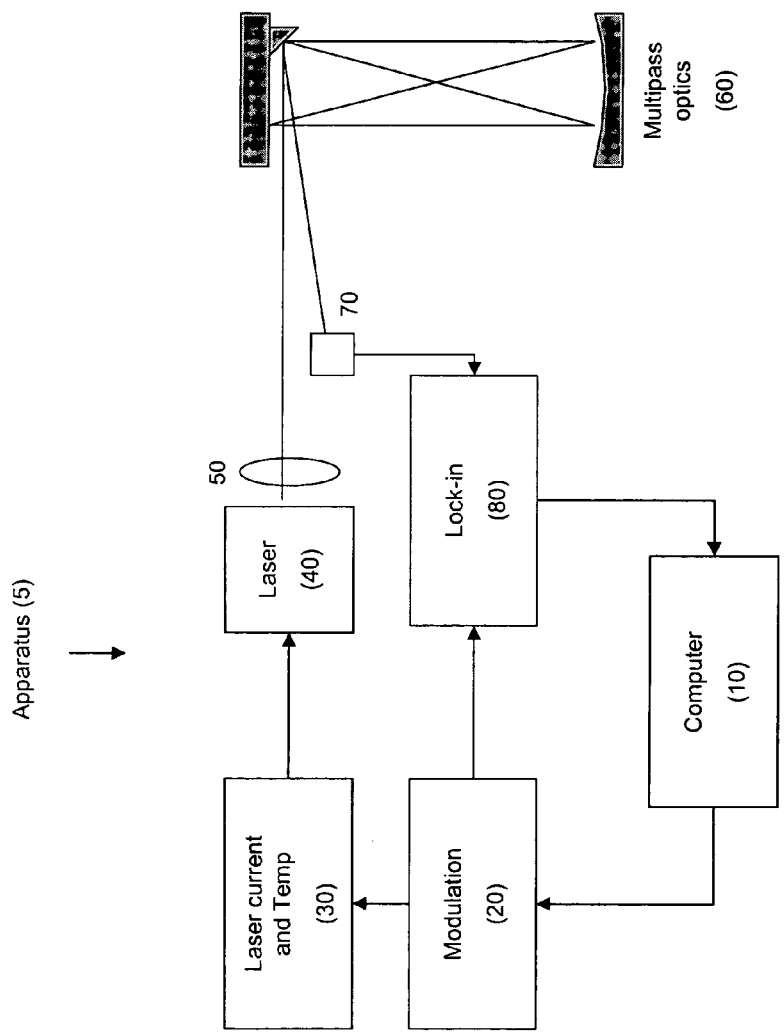
FIG. 4 shows a diode laser spectrometer. A computer loads the waveform of FIG. 3 into the digital memory of a digital waveform synthesizer (modulation). The waveform synthesizer modulates the diode laser current through a control input on a diode laser current and temperature controller. Light from the laser is collimated and directed through a multipass cell onto a detector. The photo current from the detector is measured using a lock-in amplifier that is referenced to the modulation frequency of the waveform synthesizer. The computer can record the spectrum using a digital to analog converter to generate a ramp signal, which can be added to the modulation waveform, and an analog to digital converter which can read the output of the lock-in amplifier.

The elements of a diode laser spectrometer 5 according to the invention are shown in FIG. 4. The spectrometer consists of optical and electronic components. The optical path begins with a laser 40, preferably a 1560 nm diode laser (NLK1556STK, NEL, Japan), which is provided by the manufacturer in a package that includes a thermoelectric cooler, a thermistor, a photodiode and the laser coupled through an optical isolator 50 into a single mode optical fiber, a 1×2 fiber splitter that divides the laser into a sample path and a reference path. Each path is preferably collimated using a length of optical fiber to which is fused a gradient index (e.g., an F-Col_9-15, Newport, Irvine Calif.). The sample path includes a curved mirror for further collimating the light and accurately directing the beam into a multipass cell 60 built according to the method of Herriott, and a photodiode 70 for converting the light power into an electrical current. For clarity, FIG. 4 does not show the entire reference leg. The multipass cell is enclosed in an aluminum housing with a glass window to admit the laser beam. The multipass cell holds the sample gas to be measured. The reference path from the fiber splitter passes through a 10 cm long glass cell containing carbon monoxide and directly onto a second photodiode 70. The electrical components include a laser current and temperature controller 30 (e.g., an LDC 3722, ILX, Bozeman Mont.), and an arbitrary waveform generator 20 for producing the modulation waveform (e.g., a DS 340, Stanford Research System, Palo Alto Calif.). Both the sample and reference detectors are connected to preamplifiers and then to the inputs of lock-in amplifiers (or radio frequency mixers) 80 (e.g., models SR830 and SR510). The preamplifier outputs are also connected to the inputs of a pair of RC low pass filters that measure the dc component of the photocurrent. Finally, the system includes a computer 10 with a series of analog to digital inputs and digital to analog outputs and an IEEE 488 interface.

The modulation waveform is added to a slower current ramp using a resistor network, and the sum is used to modulate the laser current via the modulation port of the current controller. The slow ramp sweeps the laser wavelength over a range that includes an absorption feature of carbon dioxide and carbon monoxide. The transfer function from scan voltage to laser wavelength was calibrated separately and is nearly linear. The ramp serves as a surrogate for the spectral wavelength axis in the spectra that are recorded. It is generated in stair-step fashion by the digital to analog output of the computer interface.

Before the measurement is made, the desired waveform is downloaded from the computer to the waveform generator over the IEEE 488 interface. In operation, the waveform generator must be phase-locked to the reference for the lock-in amplifier. This is accomplished in the present instance in one of two ways. When operating in wavelength modulation spectroscopy mode, in which the lock-in demodulation frequency is a harmonic of the basic modulation frequency, the waveform generator is operated in continuous mode and the reference output of the waveform generator is connected to the reference input of both lock-ins. 2f detection mode of the lock-in is selected in this case, although other harmonics could be used. When operating in tone burst mode, for which the lock-in demodulation frequency is a sub-harmonic of the basic modulation frequency, the waveform generator is set to produce one tone burst cycle after each trigger. The trigger is the reference output of the DS 340 lock-in, which also drives the reference input of the SR510 lock-in. In tone burst mode both lock-ins are set to 1f detection mode.

The X outputs of the lock-in amplifiers are digitized and stored once at each step in the computer-generated ramp.

To measure the sensitivity of the modulation techniques to different fringes, the optical set-up is modified. Instead of sending the laser light to the multipass cell, it is sent to the input of a Michelson interferometer. By adjusting the position of a movable mirror, it is straightforward to create strong interference fringes of known free spectral range. The fringe sensitivity is determined by measuring the peak to trough amplitude of the fringe observed by modulation techniques to the peak to trough amplitude measured in the dc path with the modulation turned off. This ratio measurement accounts for variations in the fringe amplitude that may occur when the movable mirror is set to a new position. The symbols show the sensitivity determined for standard wavelength modulation in FIG. 2($a$), wavelength modulation using the optimized envelope in FIG. 2($b$), and tone burst modulation using the optimized envelope in FIG. 2($c$).

These examples focus on wavelength modulation with second harmonic detection and tone burst modulation using diode laser spectroscopy. This technique could be extended to wavelength modulation with detection at other harmonics, to frequency modulation spectroscopy where the modulation frequency or depth could be varied, to tone burst spectroscopy where the modulation frequency is in the fms limit, or to the use of non-sinusoidal modulation waveforms such as square wave, quasi-square wave, or triangle wave modulation. The light source could be a laser or other light source with a spectral width less than or equal to the width of the spectral feature to be detected, and with the capability to modulate the wavelength or frequency. For example, a solid state laser could be used with an electro-optic modulator to provide the frequency modulation. The modulation waveform could be generated by digital or analog means.

To summarize, envelope functions can take many forms. In the usual case of use of a single modulation waveform having constant amplitude (e.g., sine wave (typical), square wave, triangle wave), the envelope function has a period that is longer than the modulation but shorter than the time constant. The applied modulation is equal to the product of a constant high frequency modulation times a lower frequency envelope. An appropriate envelope function according to the invention can be expanded in a Fourier series and when so expanded has a constant term and at least two Fourier components. For tone burst modulation, one detects at the frequency of the envelope function instead of the high frequency, but that does not define the envelope. In fact, one can even have a tone burst case with a still longer envelope that is shorter than the time constant but is not related to the detection frequency. Envelope functions according to the invention do not include two special cases: one in which the envelope function is a sine wave plus a constant (Cassidy and Reid "jitter modulation" and Gallagher two-tone) and one in which the envelope is a square wave from zero to a set value (conventional tone burst modulation).

Accordingly, for purposes of the specification and claims, an "envelope function" is defined as follows: a function that when expressed as a Fourier series includes at least two non-zero frequency components, and when expressed as a Hadamard series (a binary version of a Fourier series) includes at least two non-zero components.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A spectrometer comprising:
   a light source;
   a modulator modulating said light source with a carrier waveform multiplied by an envelope function;
   a sample region;
   a photodetector;
   a light path from said light source through said sample region and to said photodetector; and a demodulator demodulating current from said photodetector at a reference frequency whereby one or more etalon fringes are minimized, wherein a shape of said envelope function operates to selectively detect predetermined Fourier components of a spectrum, said envelope function comprises a polynomial function of order greater than two, and a period of said envelope function is at least as long as a time constant employed by said demodulator.

2. The spectrometer of claim 1 wherein said reference frequency of said demodulator is equal to a frequency of said carrier waveform or an integer multiple thereof.

3. The spectrometer of claim 1 wherein said reference frequency of said demodulator is equal to a frequency of said envelope function.

4. The spectrometer of claim 1 wherein said light source is a laser.

5. The spectrometer of claim 4 wherein said light source is a diode laser.

6. The spectrometer of claim 1 wherein said demodulator comprises a lock-in amplifier.

7. The spectrometer of claim 1 wherein said demodulator comprises an radio frequency mixer.

8. A spectrometry method comprising the steps of:
 modulating a light source with a carrier waveform multiplied by an envelope function;
 directing light from the light source through a sample region and to a photodetector; and
 demodulating current from the photodetector at a reference frequency whereby one or more etalon fringes are minimized, wherein a shape of said envelope function operates to selectively detect predetermined Fourier components of a spectrum, said envelope function comprises a polynomial function of order greater than two, and a period of said envelope function is at least as long as a time constant employed by said demodulator.

9. The method of claim 8 in the demodulating step the reference frequency is equal to a frequency of the carrier waveform or an integer multiple thereof.

10. The method of claim 8 in the demodulating step the reference frequency is equal to a frequency of the envelope function.

11. The method of claim 8 wherein the light source is a laser.

12. The method of claim 11 wherein the light source is a diode laser.

13. The method of claim 8 wherein the demodulating step comprises employing a lock-in amplifier.

14. The method of claim 8 wherein the demodulating step comprises employing an radio frequency mixer.

15. A method for computing a modulation waveform, the method comprising the steps of:
 specifying a target detection efficiency in a Fourier space;
 computing a response of a waveform that comprises a carrier wave multiplied by an envelope function; and
 modifying the envelope function using nonlinear optimization means to minimize a difference between the computed response and a predetermined target gain spectrum whereby one or more etalon fringes are minimized by the modulation, wherein a shape of said envelope function operates to selectively detect predetermined Fourier components of a spectrum, said envelope function comprises a polynomial function of order greater than two, and a period of said envelope function is at least as long as a time constant employed by said demodulator.

16. The method of claim 15 wherein in the modifying step the target gain spectrum comprises a signal band and a stop band.

* * * * *